US00PP12646P2

(12) United States Plant Patent
Bunnik

(10) Patent No.: US PP12,646 P2
(45) Date of Patent: May 28, 2002

(54) BROMELIAD PLANT NAMED 'GUZ 227'

(75) Inventor: Ronald Bunnik, Pynacker (NL)

(73) Assignee: Kent's Bromeliad Nursery, Inc., Vista, CA (US)

( * ) Notice: Subject to any disclaimer, the term of this patent is extended or adjusted under 35 U.S.C. 154(b) by 7 days.

(21) Appl. No.: 09/688,889

(22) Filed: Oct. 16, 2000

(51) Int. Cl.[7] ..... A01H 5/00
(52) U.S. Cl. ..... Plt./371
(58) Field of Search ..... Plt./371, 370

*Primary Examiner*—Bruce R. Campell
*Assistant Examiner*—June Hwu
(74) *Attorney, Agent, or Firm*—James A. Lucas; Driggs, Lucas, Brubaker & Hogg Co., L.P.A.

(57) ABSTRACT

A Bromeliad hybrid comprising an improvement over its parent, Guzmania 'Irene'. The foliage is denser and more compact than that of 'Irene', and the leaves are darker, thicker and wider. The plant is a tetraploid, and is faster growing than 'Irene', reaching marketability in 10–12 months. The primary bracts are wider and closer together making the spike fuller and more compact. The bract color is darker and clearer than that of 'Irene'.

1 Drawing Sheet

BACKGROUND OF THE INVENTION

This application relates to a newly developed interspecific hybrid Guzmania plant resulting from a planned breeding program that is conducted on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Additional objects of the breeding program are to produce plants of the Bromeliaceae family which will be attractive to the consumer; which will develop reasonably rapidly under controlled conditions; and, retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant was a sport of Guzmania 'Irene' (unpatented) which is the progeny resulting from the cross of *Guzmania lingulata* 'Equador' (unpatented)×*Guzmania wittmackii*, 'Pink Equador' (unpatented). This particular sport was about 1¼ years old when discovered by me growing at a nursery under my control in Pynacker, Holland. With the recognition that this sport satisfied the objects of the breeding program, the sport was isolated and set aside for further observation and testing. The resulting selection has been assigned the designation 'GUZ 227' for purposes of identification. This plant has been reproduced by tissue culture at Evergem Belgium, and the clonal specimens resulting therefrom have been determined to be identical to the original selection in all distinguishing characteristics. The distinctive attributes of this plant will be revealed in the Summary of the Invention and the Botanical Description to follow.

SUMMARY OF THE INVENTION

The attributes of the plant 'GUZ 227' which distinguish it from the other similar Guzmania hybrids are described as follows:

This hybrid represents a marked improvement over the Guzmania 'Irene'. The foliage of 'GUZ 227' is denser and more compact than 'Irene' with darker, wider and thicker leaves. The plant grows faster than 'Irene' with a broader overall width. The primary bracts are closer together making the floral spike more compact. The upper primary bracts are more horizontal, giving the spike a more symmetrical appearance. The individual bracts are broader giving the floral spike a fuller appearance. The color of the bract is darker and clearer than the bract of Guzmania 'Irene' of which it is derived. 'GUZ 227' grows more rapidly than Guzmania 'Irene', growing from liner to marketability in 10–12 months.

This hybrid holds its color well for 3 to 4 months under interior lighting conditions.

No unusual susceptibility to diseases of Guzmania has been noted.

BRIEF DESCRIPTION OF THE DRAWING

The single color photograph of the drawing depicts a mature 1¼ years old specimen of the plant in mid to late flowering stage. Illustrated are the mature leaves, scape bracts and primary bracts. The color definitions in the specification have been taken from The R.H.S Colour Chart of The Royal Horticultural Society. The colors depicted are believed to be of a high level of color fidelity and are believed to be as close to the actual coloration of the plant as possible in a photographic illustration of this quality. However, due to factors such as light reflectance, cultural conditions and horticultural practices, the coloration of this plant should be understood to be approximate. For example, the bract color might slightly fade if the plant is subjected to bright light and the leaf color may vary depending on the composition and the concentration of fertilizer which may be applied to the plant.

BOTANICAL DESCRIPTION OF THE PLANT

Plant classification:

*Botanical.*—*Guzmania lingulata*×*G. wittmackii* 'Irene'.

*Commercial.*—Flowering tropical plant of the Guzmania market class.

Parentage: Sport of Guzmania 'Irene'.

Propagation:

*Method of asexual reproduction.*—Tissue culture.

*Where reproduction took place.*—Reginald De Roose BVBA DROOGTE 139, B9940 Evergem, Belgium.

Plant: Type—monocot perennial; tetraploid.

*General characteristics.*—Large in size. Overall height from soil surface including inflorescence—19" to 21". Overall width—32" to 34". Vase formed.

*Hardiness at temperatures below 32° F.*—Tender.

Leaves:

*Number.*—20–23.

*Large in size.*—Length 23"–25"; Width: 1¾" (mid length).

*Shape.*—lanceolate; arching, recurved at tips which are abruptly pointed.

*Thickness.*—Thick.

*Margin.*—Smooth.

Apetiolate:

*Coloration.*—RHS 147-A obverse and RHS 146-A reverse, minor staining and lineation on RHS 61-A obverse and reverse, particularly on upper leaves and leaf base.

*Texture.*—Glabrous, obverse and reverse.

Inflorescence a branched spike: Tender, large and long conic appressed upper bracts.

Scape bracts:

*Size.*—17½"×2¼' to 8¾"×1¾" at the apex;

*Shape.*—Lanceolate terminating in narrowly acute tip.

*Number.*—18–22.

*Color.*—Base to apex RHS 147-A obverse and RHS 147-B reverse; Lower bracts stained 61-A obverse and reverse, blending into all RHS 61-A at apex; Some upper bracts tipped RHS 137-A.

*Texture.*—Glabrous, obverse and reverse.

Primary bracts:

*Size.*—10"×2¼" to ¾"×1¼".

*Color.*—Lower bracts—RHS 146-D obverse and reverse at base blending into RHS 61-A obverse and reverse, RHS 147-A at tip. Progressing upward, base of bracts become RHS 146-D obverse and reverse with tips losing their 147-A coloration and becoming RHS 61-A obverse and reverse. Base of top bracts are colored RHS 154-D obverse and RHS 149-B reverse, and tips are stained RHS 61-A obverse and reverse.

*Shape.*—Lanceolate, narrowly acute.

*Attitude.*—Gradual transition from ascending lower bracts to nearly horizontally flaring apex bracts.

*Texture.*—Glabrous, obverse and reverse.

Flowers: Clusters glomerule.

Medium-large in size.—Sepals ⅞"×3/16" translucent, 3 in number; color RHS 151-D, loses color at tips (very translucent). Petals 1½"×¼" translucent; color paler than RHS 150-D; 3 in number; scarcely open at anthesis.

*Corolla.*—Cylindrical.

Fruit: A three celled capsule splitting longitudinally when mature, Sterile hybrid Seeds with pappus-seeds not viable.

Resistance/susceptiblity to disease and pests: None observed

Floral buds: Pyramidal in shape.

*Size.*—2.75" long by 1.25" wide.

*Color.*—1C at the base fading to 2D at tip.

*Sepals.*—3 in number. Size—1.25" long by 0.25" wide. Color—1D.

*Petals.*—3 in number. Size—1.25" long by 0.25" wide.

Reproductive organs:

*Stamens.*—6 in number. Color: 1C. Length—0.75".

*Anthers.*—Color: 1C. Length: 0.25".

*Filaments.*—Color: 1D. Length: 0.5".

*Pollen.*—Color: 1D.

*Pistil.*—Number 1. Color: 2D.

*Stigma.*—Color: 2D. Size: length—1.8"; Width — 1/16".

*Style.*—Color—2A. Length: ¾".

What is claimed is:

1. A new and distinct variety of Guzmania plant named 'Guz 227' as illustrated and described herein.

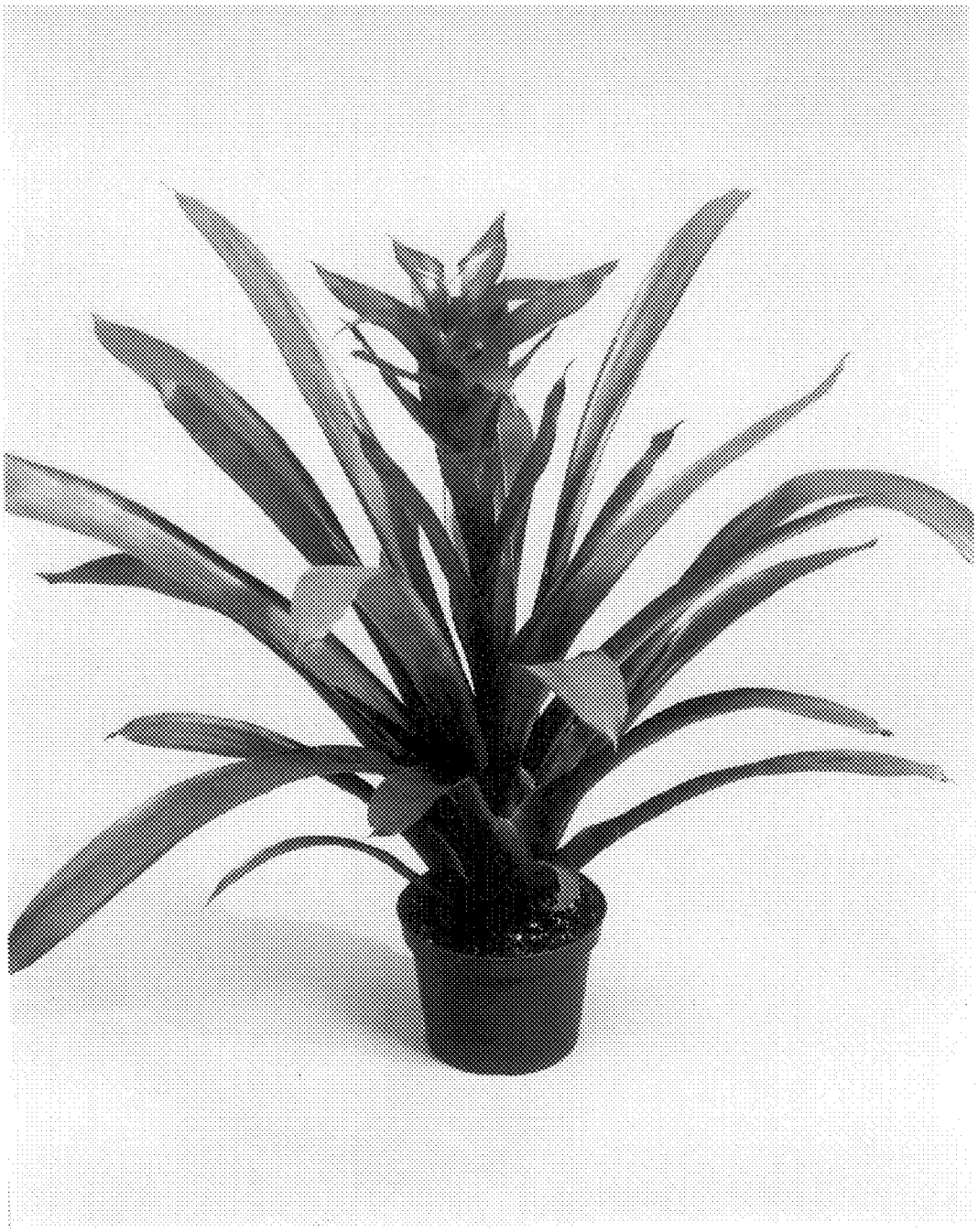

* * * * *